(12) United States Patent
Meyers et al.

(10) Patent No.: US 6,383,475 B1
(45) Date of Patent: May 7, 2002

(54) BREATH FRESHENING LIPSTICK

(75) Inventors: Alan Joel Meyers, Trumbull; Celeste Anne Lutrario, Hamben; Marianne Elliott, Trumbull, all of CT (US); Lee Ann Gallagher, Morristown, NJ (US)

(73) Assignee: FD Management, Inc., Wilmington, DE (US)

( * ) Notice: Subject to any disclaimer, the term of this patent is extended or adjusted under 35 U.S.C. 154(b) by 0 days.

(21) Appl. No.: 09/437,520

(22) Filed: Nov. 10, 1999

Related U.S. Application Data

(60) Provisional application No. 60/129,781, filed on Apr. 16, 1999.

(51) Int. Cl.[7] ............................. A61K 6/00; A61K 7/00; A61K 7/025
(52) U.S. Cl. ......................................... 424/64; 424/401
(58) Field of Search .................... 424/64, 401

(56) References Cited

U.S. PATENT DOCUMENTS

| | | | |
|---|---|---|---|
| 4,029,759 A | * 6/1977 | Humbert et al. | 424/49 |
| 4,267,166 A | 5/1981 | Yajima | 424/48 |
| 4,892,890 A | 1/1990 | Damani | 514/784 |
| 5,085,715 A | 2/1992 | Lukas et al. | 424/145 |
| 5,085,856 A | 2/1992 | Dunphy et al. | 424/64 |
| 5,108,737 A | 4/1992 | Dunphy et al. | 424/64 |
| 5,300,305 A | * 4/1994 | Stapler et al. | 424/490 |
| 5,310,547 A | 5/1994 | Dunphy et al. | 424/64 |
| 5,407,921 A | 4/1995 | Katsuragi et al. | 514/75 |
| 5,514,367 A | 5/1996 | Lentini et al. | 424/59 |
| 5,543,148 A | 8/1996 | Lapidus | 424/401 |
| 5,571,782 A | 11/1996 | Trinh et al. | 512/4 |
| 5,626,837 A | 5/1997 | Shimada et al. | 424/49 |
| 5,635,238 A | 6/1997 | Trinh et al. | 426/650 |
| 5,695,746 A | 12/1997 | Garlick, Jr. et al. | 424/49 |
| 5,696,169 A | 12/1997 | Otsu et al. | 514/675 |

FOREIGN PATENT DOCUMENTS

| | | |
|---|---|---|
| DE | 39 13 120 | 4/1989 |
| DE | 196 21 575 | 5/1996 |
| EP | 0 549 267 | 6/1993 |
| EP | 0 803 243 | 4/1997 |
| GB | 2 090 738 | 12/1981 |
| JP | 10017434 | 1/1998 |
| WO | 95/03709 | 2/1995 |

OTHER PUBLICATIONS

Ito et al., "Cosmetics containing menthol derivatives", Chemical Abstract 122:169701, 1993.*
Chemical Abstract 112:25370.
Chemical Abstract 112:83839.
Chemical Abstract 113:197644.
Chemical Abstract 122:169701.
Copy of Almay Stay Smooth Anti–Chap Color™ packaging box.

* cited by examiner

Primary Examiner—Thurman K. Page
Assistant Examiner—S. Howard
(74) Attorney, Agent, or Firm—Abelman, Frayne & Schwab

(57) ABSTRACT

A lipstick is provided for freshening the breath and reducing oral malodor. These lipsticks are based on a combination of free menthol and a bound menthol substance, the latter being either a complex or an encapsulated form. Most preferred is a menthol complex with beta-cyclodextrin. Further components of the lipstick include lipophilic material such as waxes and usually colorants. Water is advantageously included at levels ranging up to 10% by weight.

4 Claims, No Drawings

BREATH FRESHENING LIPSTICK

The instant application claims benefit of the provisional application 60/129,781 filed Apr. 16, 1999.

BACKGROUND OF THE INVENTION

1. Field of the Invention

The invention concerns a lipstick for freshening breath and controlling oral malodor.

2. The Related Art

Foods and natural decay generate odors within the oral cavity. These are apt to remain on the breath long after meals. Particular offenders in the food category are liquors, garlic, fish and leeks. Smoking also generates smells. Foul breath sometimes arouses unpleasant responses in those near the generating source. Malodor is also an indication of oral and other body organ illnesses.

Traditionally bad breath has been inhibited through use of toothpaste and oral rinses. Application of these products ordinarily requires a wash facility. Use of these products is practiced most often only just subsequent to a meal. Protection may not linger for long periods between meals, especially where brushing or rinsing opportunities are unavailable.

Accordingly, it is an object of the present invention to provide products for freshening breath and reducing oral malodor which are effective for relatively long periods of time.

Another object of the present invention is to provide products for freshening breath and reducing oral malodor which are easy to apply and require no wash facilities for their application.

These and other objects of the present invention will become more readily apparent from consideration of the following summary and detailed discussion.

SUMMARY OF THE INVENTION

A lipstick is provided for freshening breath and controlling oral malodor, the lipstick including:

(i) from about 10 to about 99% of lipophilic material;
(ii) from about 0.01 to about 2% of free menthol; and
(iii) from about 0.1 to about 10% of a bound menthol substance.

DETAILED DESCRIPTION OF THE INVENTION

Now it has been found that breath freshening and the reduction of oral malodor is achievable through a specially formulated lipstick. Unlike toothpaste and mouth rinses, the specially formulated lipsticks of the present invention require no basin or running water for their application. They also release a constant stream of oral malodor reductant for extended periods of time. Free menthol combined with a bound menthol substance serve as the actives. During periods just subsequent to application of the lipstick, the free menthol is released to the oral cavity. As free menthol concentration within the lipstick decreases, the bound menthol substance begins to release its menthol component therefore extending the activity period.

By the term "free menthol" is meant menthol uncomplexed, unbound and non-encapsulated (other than being within the general lipophilic material matrix). Amounts of free menthol may range from about 0.01 to about 2%, preferably from about 0.05 to about 1%, optimally from about 0.1 to about 0.5% by weight.

By the term "bound menthol substance" is meant a physical combination of free menthol releasably complexed or encapsulated by a binding or enrobing substance. Materials suitable as encapsulate include polysaccharides such as starch or modified starch; synthetic polymers and copolymers such as polyvinyl alcohol, acrylics or polyurethanes; vegetable gums such as gelatin, guar or carrageenan gums, and combinations thereof.

Complexes of menthol may be formed with starches such as cyclodextrin, clathrates, clays and zeolites. Most preferred are complexes of menthol with cyclodextrin. By the term "cyclodextrin" is meant any of the known natural cyclodextrins as well as substituted and unsubstituted analogs and any of their derivatives. Examples of derivatives include methyl-beta-cyclodextrin, hydroxyethyl-beta-cyclodextrin and hydroxypropyl-beta-cyclodextrin. Generically these substances are cyclic oligosaccharides with capability of forming inclusion complexes with a variety of materials. They vary in ring size from 6 to 12 glucose units. The most common are the 6, 7 or 8 glucose built rings commonly referred to as alpha-cyclodextrin, beta-cyclodextrin and gamma-cyclodextrin, respectively. These substances are available from the Lipo Chemical Company, a subsidiary of Cerestar Inc. (formally the American Maize Company). A complex of menthol with beta-cyclodextrin is the most preferred embodiment.

Amounts of the bound menthol substance may range from about 0.1 to about 10%, preferably from about 0.2 to about 2%, optimally from about 0.5 to about 1% by weight based on releasable menthol by weight of the lipstick composition.

An adjunct freshening component to menthol is that of anethole present in respective weight ratio of about 100:1 to about 1:1, preferably from about 50:1 to about 2:1, optimally from about 30:1 to about 10:1.

An essential element of all lipsticks is that of lipophilic material. These materials may be solids (defined as being firm and of a plastic texture at room temperature) and liquids, although the combination thereof should provide structure to the lipstick rendering same as a solid with plastic texture at room temperature.

Liquids suitable as components of the lipophilic materials may be those selected from the group consisting of hydrocarbon oils, fatty acid esters, fatty alcohols and mixtures thereof. Hydrocarbon oils may be either natural or synthetically produced. Those from mineral sources include petroleum derived mineral oils, petrolatum and mixtures thereof. Plant sourced oils include saturated and unsaturated fatty acids examples of which are adipic, caprylic, capric, lauric, myristic, palmitic, stearic acids and mixtures thereof. Unsaturated fatty acids include linoleic, linolenic, ricinoleic, oleic, elaidic, erucic acids and mixtures thereof. Other vegetable oils include castor bean oil, rapeseed oil, soybean oil, palm kernel oil, babassu kernel oil, coconut oil and mixtures thereof. Fatty alcohols suitable for this invention include cetearyl alcohol, cetyl alcohol, myristyl alcohol, stearyl alcohol, isostearyl alcohol, lanolin alcohol, lauryl alcohol, oleyl alcohol and mixtures thereof. Fatty acid esters suitable for this invention may be derived from the esterification reaction of $C_8$–$C_{20}$ fatty acids reacted with $C_1$–$C_{20}$ monohydric and polyhydric alcohols (the latter being triglycerides). Illustrative but not limiting examples include cetyl ricinoleate, glycerol oleate, glycerol monostearate, isopropyl lanolate, isopropyl linoleate, isopropyl myristate, ethyl palmitate, isopropyl palmitate, isopropyl isostearate and mixtures thereof.

Solid lipophilic materials are generally those having melting points from about 55° C. to about 110° C. The solids may include fatty alcohols, fatty acid esters, waxes and mixtures thereof. Substances mentioned under the liquids category having the suitable aforementioned melting point range should be considered as solid lipophilic materials. Waxes are a particularly useful type of solid within the context of the present invention. Preferred waxes include those selected from the group consisting of candelilla, beeswax, carnauba, spermaceti, montan, ozokerite, ceresin, paraffin, modified beeswax, bayberry wax, castor wax, microcrystalline waxes and mixtures thereof.

Amounts of the lipophilic material may range from about 10 to about 99%, preferably from about 30 to about 90%, optimally from about 40 to about 80% by weight of the composition.

Advantageously, compositions of this invention will include an antibacterial agent present in amounts from about 0.05 to about 10%, preferably from about 0.2 to about 5%, optimally from about 0.8 to about 3% by weight. Suitable as antibacterial agents are zinc salts, quaternary ammonium compounds and chlorinated hydrocarbons. Illustrative of the quaternary ammonium compounds are pyridinium salts (such as cetyl pyridinium chloride) and benzalkonium salts (such as dimethyl benzylammonium chloride) and chlorhexidines. Illustrative of the chlorinated hydrocarbons are salicylanides (such as 4', 5-dibromosalicylanlide) and halogenated diphenyl ethers such as 2,4,4'-trichloro-2'-hydroxydiphenyl ether (commonly known as trichlosan).

Most preferred as the antibacterial agent are zinc salts. Examples of zinc salts that may be employed are those having organic and inorganic anions selected from the group consisting of acetate, benzoate, borate, bromide, carbonate, citrate, chloride, glycerophosphate, hexafluorosilicate, di-lactate (trihydrate), nitrate, phenolsulfonate, glycinate, silicate, alkanoates having 8 to 18 carbon atoms, such as zinc stearate, salicylate, stannate, sulfate, tannate, titanate, tetrafluoroborate, tartrate and mixtures thereof. The zinc salts may be used singly or in admixture.

By the term "zinc salt" is meant any zinc compound capable of dissociating into zinc ions at a temperature of about 37° C., as well as to zinc ions formed in aqueous medium such as a mouthwash or oral salivary secretions. Most preferred for purposes of the present invention is zinc citrate such as hydrated zinc citrate. Zinc compounds such as zinc oxide are outside the scope of the zinc salt class.

Advantageously lipsticks of the present invention may contain a small amount of water. Small amounts are useful as solubilization systems for the free menthol so that it may be delivered more readily to the oral cavity as the user wets their lips with the tongue and portions of saliva. Too high levels of water are undesirable because of the incompatibility with the lipophilic materials that forms the vast majority of the lipstick. Suitable amounts of water may range from about 0.1 to about 25%, preferably from about 1 to about 10%, optimally from about 3 to about 8% by weight of the composition.

Small amounts of water are also useful with respect to releasing menthol from the bound menthol mixtures. Water soluble complexing agents such as cyclodextrin or encapsulating agents such as polyvinyl alcohol are soluble in water. The small amount of water dissolves encapsulating material or acts as a transfer media for menthol complexed cyclodextrins.

A variety of antioxidants can further assist in reacting with malodor generating substances found in the mouth. Suitable antioxidants are those selected from green tea, Vitamin C and its derivatives (e.g. ascorbyl palmitate, magnesium ascorbate and tetraisopropyl ascorbate), chamomile, tocopherol and its derivatives (e.g. tocopheryl palmitate), butylated hydroxytoluene, oryzanol and mixtures thereof. Amounts of the antioxidants may range from about 0.0001 to about 5%, preferably from about 0.01 to about 2%, optimally from about 0.1 to about 1.5% by weight.

Skin protective agents may also be included in lipsticks of the present invention. These include anti-aging substances such as alpha-hydroxy acids, beta-hydroxy adds and esters thereof (e.g. tridecylsalicylate), retinol and retinoid esters (e.g. retinyl linoleate). Amounts of these substances may range from about 0.001 to about 5%, preferably from about 0.1 to about 1% by weight.

Polysaccharides may also be incorporated into the lipstick compositions of this invention. Suitable polysaccharides include sorbitol available as Neosorb™ and Trehalose. Amounts of the polysaccharide may range from about 0.1 to about 10%, preferably from about 0.5 to about 2% by weight.

Emulsifiers may be incorporated into the lipstick compositions of the present invention. Overall concentration of emulsifier may range anywhere from about 0.1 to about 30% by weight of the formulation, preferably from about 0.5 to about 20%, optimally between about 2 and 10% by weight.

Phospholipids is an important category of emulsifier that may contribute to the stability and pleasing appearance of the composition. Examples of phospholipids are those within the categories of phosphoglycerides, lysophosphoglycerides, sphingomyelins and mixtures thereof. Especially useful as a phospholipid is lecithin.

Fatty acid derivative-type emulsifiers may also be employed, especially in combination with a phospholipid. These emulsifiers may include monoacyl glycerol, diacyl glycerol and polyglycerol esters and combinations thereof. Especially preferred are glycerol monoalkanoates, an example of which are the monoglycerides of sunflower seed oil and of palm oil.

Colorants may also be included in compositions of the present invention. These substances are normally FD&C approved dyes, pigments and mixtures thereof. Illustrative are those substances selected from the group consisting of lake dyes, micas or pearls, iron oxides, titanium oxides, calcium carbonates and mixtures thereof. Particularly suitable are lakes encompassing either a pigment that is extended or reduced with a solid diluent or an organic pigment that is prepared by the precipitation of water-soluble dye on an absorptive surface, usually an aluminohydrate. Typical Aluminum Lakes are Yellow #6 Aluminum Lake, Yellow #10 Aluminum Lake, Orange #5 Aluminum Lake, Blue #1 Aluminum Lake, Red #3 Aluminum Lake, Red #27 Aluminum Lake and mixtures thereof. Calcium and barium lakes may also be employed. Bismuth oxychloride is a further useful colorant.

Sunscreens may also be incorporated into lipstick compositions of the present invention. Amounts of the sunscreens may range from about 1 to about 30% by weight of the composition. Organic and inorganic substances may serve as sunscreens. The organic substances will absorb light in the wavelength range from about 270 to about 400 nm. Illustrative examples include benzophenone 3, octyl-methoxycinnamate (Parsol MCX®), avobenzene commercially available as Parsol 1789® (from Givaudan-Roure Corporation) and mixtures thereof. Inorganic sunscreens include micronized titanium dioxide and zinc oxides.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLES 1–10

Lipsticks of the present invention are prepared according to the following compositions.

TABLE I

| INGREDIENT | \multicolumn{10}{c}{EXAMPLES} |
|---|---|---|---|---|---|---|---|---|---|---|
|  | 1 | 2 | 3 | 4 | 5 | 6 | 7 | 8 | 9 | 10 |
| Phase A |  |  |  |  |  |  |  |  |  |  |
| Castor Oil | 16.33 | 16.33 | 16.33 | 16.33 | 16.33 | 16.33 | 16.33 | 16.33 | 16.33 | 16.33 |
| Ozokerite | 3.10 | 3.10 | 3.10 | 3.10 | 3.10 | 3.10 | 3.10 | 3.10 | 3.10 | 3.10 |
| Carnauba | 1.00 | 1.00 | 1.00 | 1.00 | 1.00 | 1.00 | 3.00 | 3.00 | 3.00 | 3.00 |
| Candelillate | 4.20 | 4.20 | 4.20 | 4.20 | 4.20 | 4.20 | 4.20 | 4.20 | 4.20 | 4.20 |
| Beeswax | 3.36 | 3.36 | 3.36 | 3.36 | 3.36 | 3.36 | 3.36 | 3.36 | 3.36 | 3.36 |
| Lanolin Ultra | 5.00 | 5.00 | 5.00 | 5.00 | 5.00 | 5.00 | 5.00 | 5.00 | 5.00 | 5.00 |
| Softisan 649 ® (Triglyceride Wax) | 4.00 | 4.00 | 4.00 | 4.00 | 4.00 | 4.00 | 4.00 | 4.00 | 4.00 | 4.00 |
| Butylated Hydroxytoluene | 0.18 | 0.18 | 0.18 | 0.18 | 0.18 | 0.18 | 0.18 | 0.18 | 0.18 | 0.18 |
| Hydroxylated Lanolin | 0.50 | 0.50 | 0.50 | 0.50 | 0.50 | 0.50 | 0.50 | 0.50 | 0.50 | 0.50 |
| Mango Butter | 2.00 | 2.00 | 2.00 | 2.00 | 2.00 | 2.00 | 2.00 | 2.00 | 2.00 | 2.00 |
| Tridecyl Salicylate | 0.50 | 0.50 | 0.50 | 0.50 | 0.50 | 0.50 | 0.50 | 0.50 | 0.50 | 0.50 |
| Rice Bran Oil | 3.00 | 3.00 | 3.00 | 3.00 | 3.00 | 3.00 | 3.00 | 3.00 | 3.00 | 3.00 |
| Triisostearyl Citrate | 12.30 | 12.30 | 12.30 | 12.30 | 12.30 | 12.30 | 12.30 | 12.30 | 12.30 | 12.30 |
| Parsol MCX ® | 7.00 | 7.00 | 7.00 | 7.00 | 7.00 | 7.00 | 7.00 | 7.00 | 7.00 | 7.00 |
| Benzophenone 3 | 4.00 | 4.00 | 4.00 | 4.00 | 4.00 | 4.00 | 4.00 | 4.00 | 4.00 | 4.00 |
| Tocopherol | 1.50 | 1.50 | 1.50 | 1.50 | 1.50 | 1.50 | 1.50 | 1.50 | 1.50 | 1.50 |
| Sunflower Monoglycerides | 3.50 | 3.50 | 3.50 | 3.50 | 3.50 | 3.50 | 3.50 | 3.50 | 3.50 | 3.50 |
| Lecithin | 1.00 | 1.00 | 1.00 | 1.00 | 1.00 | 1.00 | 1.00 | 1.00 | 1.00 | 1.00 |
| Phase B |  |  |  |  |  |  |  |  |  |  |
| Oryzanol | 0.25 | 0.25 | 0.25 | 0.25 | 0.25 | 0.25 | 0.25 | 0.25 | 0.25 | 0.25 |
| Rice Starch | 3.00 | 3.00 | 3.00 | 3.00 | 3.00 | 3.00 | 3.00 | 3.00 | 3.00 | 3.00 |
| Phase C |  |  |  |  |  |  |  |  |  |  |
| Red #6 | 2.40 | — | 2.40 | 2.80 | 2.40 | 4.03 | 2.40 | 0.40 | 0.40 | — |
| Titanium Dioxide | 0.40 | 0.40 | 0.40 | 0.40 | — | 0.40 | 0.40 | 0.40 | 0.40 | 0.40 |
| Blue #1 | — | — | 0.40 | — | 0.40 | — | — | 2.40 | 2.40 | 2.80 |
| Yellow Iron Oxide | 1.63 | 4.03 | 1.23 | 1.23 | 1.23 | — | 1.63 | 1.23 | 1.23 | 1.23 |
| Phase D |  |  |  |  |  |  |  |  |  |  |
| Timica Silkwhite | 4.40 | 4.40 | 4.40 | 4.80 | 4.60 | 4.60 | 4.60 | 4.60 | 4.60 | 4.60 |
| Phase E |  |  |  |  |  |  |  |  |  |  |
| Vitamin C/Zinc Citrate (1:5) | — | 4.00 | 5.00 | 6.00 | 4.00 | 4.00 | — | — | — | — |
| Cyclodextrin-Menthol Complex | 2.00 | 2.00 | 1.00 | 1.00 | 0.80 | 0.80 | 0.80 | 0.80 | 0.80 | 0.80 |
| Menthol | 0.18 | 0.18 | 0.28 | 0.38 | 0.48 | 0.38 | 0.38 | 0.38 | 0.38 | 0.38 |
| Anethole | 0.01 | 0.01 | 0.02 | 0.02 | 0.03 | 0.02 | 0.02 | 0.02 | 0.02 | 0.02 |
| Methyl Salicyclate | 0.23 | 0.23 | 0.21 | 0.11 | — | 0.11 | 0.11 | 0.11 | 0.11 | 0.11 |
| Phase F |  |  |  |  |  |  |  |  |  |  |
| Water | 8.00 | 4.00 | 4.00 | 3.00 | 5.00 | 5.00 | 4.00 | 4.00 | 4.00 | 4.00 |
| Trehalose | 1.00 | 1.00 | 1.00 | 1.00 | 1.00 | 1.00 | 4.00 | 4.00 | 4.00 | 4.00 |
| Green Tea | 1.00 | 1.00 | 1.00 | 1.00 | 1.00 | 1.00 | 1.00 | 1.00 | 1.00 | 1.00 |
| Ginko Biloba | 0.50 | 0.50 | 0.50 | 0.50 | 0.50 | 0.50 | 0.50 | 0.50 | 0.50 | 0.50 |
| Aloe Vera Powder | 0.10 | 0.10 | 0.10 | 0.10 | 0.10 | 0.10 | 0.10 | 0.10 | 0.10 | 0.10 |
| Neosorb ® Sorbitol | 2.00 | 2.00 | 2.00 | 2.00 | 2.00 | 2.00 | 2.00 | 2.00 | 2.00 | 2.00 |
| Phase G |  |  |  |  |  |  |  |  |  |  |
| Fragrance/Flavor | 0.70 | 0.70 | 0.70 | 0.70 | 0.70 | 0.70 | 0.70 | 0.70 | 0.70 | 0.70 |

EXAMPLE 11

A biophysical oral malodor prevention study was conducted to determine the efficacy of lipsticks according to the present invention. Female panelists aged 18–65 were enrolled in the study. Twenty-nine panelists qualified to participate, each having scores above 4 (on a breath malodor scale of 1–8) on both days of a two-day trial.

Methods

Oral malodor was evaluated by two trained judges at baseline, immediately following product application (t=0), 2 hours, and 4 hours after application. Panelists were graded by breathing a slow, steady stream through a straw that was placed through a slit in a booth where each of the judges evaluated their degree of malodor on an 8 point scale.

Scoring by judges was as follows:

| GRADE | DESCRIPTOR |
| --- | --- |
| 1 | No malodor |
| 2 | Doubtful malodor |
| 3 | Slight malodor |
| 4 | Definite malodor |
| 5 | Definite malodor |
| 6 | Intense malodor |
| 7 | Intense malodor |
| 8 | Intense malodor |

Scores of 4 and 5 were relative scores indicating definite malodor, and scores of 5–8 were relative scores indicating intense malodor, but no other descriptors were given. In order for a score to be recorded, both judges needed to be within 1 scoring point of each other. A study coordinator stood behind the partition with the judges to check scores (the judges were separated by a partial wall so that they could not see each others' scores). This was so that they could tell the panelist to immediately return to a judge when both judges' scores did not match. If by the second try the scores were still not within 1 scoring point of each other, the trained study coordinator would evaluate and score that panelist.

Procedure

Four (4) panelist were randomly chosen at the start of each day to "cycle" (acclimate) the judges, which was to acclimate their olfaction before they started to grade actual baseline readings. After cycling, panelists proceeded to the grading room in groups of 4 to have their breath screened to qualify them for participation in the study. In order to qualify, they needed to score at least at 4 (definite malodor) on a scale of 1–8. Each qualified panelist was assigned randomly to apply one of the two lip products.

Products Tested

A lipstick with a composition essentially identical to that of Example 3 represented a typical composition of the present invention. As a control, a formulation identical to that of the experimental stick was evaluated except the formulation lacked menthol, menthol-cyclodextrin, zinc citrate and flavor components.

Treatment

Treatment involved application of one of the lip products (either the product or the control) on Day 1, and the other on Day 2 according to a randomization schedule. After application, panelists then proceeded in groups of four to the judging area to be graded immediately after application (t=0), 2 hours, and 4 hours after application.

Analysis

Means of the two judges' scores were obtained and analysis of changes from baseline readings was performed using Microsoft Excel 5.0 and SPSS software. The Wilcoxon Matched-Pairs Signed-Ranks Test was used to test for significance within and between treatments.

Results

Table II lists the statistical results from the study. The baseline malodor scores were not significantly different from each other. Immediately after application of the lipsticks (t=0), there was a significant decrease in malodor scores for both the control and Example 3 stick compared with the baseline scores. However, there was significantly greater decrease in malodor scores for the Example 3 stick compared against the control. Two hours after treatment, the difference between the control and Example 3 was directionally significant, and after 4 hours there was essentially no difference between the two products. Nine of the twenty-nine panelists in the study had extremely high mean baseline readings of 7.5 or 8. They were removed from the second series in Table II. With these scores removed, the malodor scores for the Example 3 stick were significantly lower than (improved over) the control at t=0, 2 hours and 4 hours.

TABLE II

Statistical Summary
Within Treatment Changes from Baseline (Before - After)

| N Obs | Time | Z | Prob>[T] |
| --- | --- | --- | --- |
| | Example 3 Lipstick | | |
| 29 | 0 Hr. - Baseline | −4.5663 | <0.0001 |
| 29 | 2 Hr. - Baseline | −4.5147 | <0.0001 |
| 29 | 4 Hr. - Baseline | −4.3035 | <0.0001 |
| | Control | | |
| 29 | 0 Hr. - Baseline | −3.9121 | 0.0001 |
| 29 | 2 Hr. - Baseline | −3.5688 | 0.0004 |
| 29 | 4 Hr. - Baseline | −3.8958 | 0.0001 |
| | Example 3 Lipstick | | |
| 20 | 0 Hr. - Baseline | −3.8595 | 0.0001 |
| 20 | 2 Hrs. - Baseline | −3.6766 | 0.0002 |
| 20 | 4 Hrs. - Baseline | −3.5017 | 0.0005 |
| | Control | | |
| 20 | 0 Hrs. - Baseline | −3.3078 | 0.0013 |
| 20 | 2 Hrs. - Baseline | −2.9839 | 0.0028 |
| 20 | 4 Hrs. - Baseline | −3.1461 | 0.0017 |

Between Treatment Changes from Baseline (Before - After)

| N Obs | Example 3 Lipstick vs. Control | Z | Prob>[T] |
| --- | --- | --- | --- |
| 29 | Tr 0 Hr - Tr Base: UT 0 Hr - UT Base | −2.4741 | 0.0134 |
| 29 | Tr 2 Hr - Tr Base: UT 2 hr - UT Base | −1.7636 | 0.0778 |
| 29 | Tr 4 Hr - Tr Base: UT 4Hr - UT Base | −1.0220 | 0.3068 |
| 20 | Tr 0 Hr - Tr Base: UT 0 Hr - UT Base | −2.5830 | 0.0098 |
| 20 | Tr 2 Hr - Tr Base: UT 2 Hr - UT Base | −3.2998 | 0.0010 |
| 20 | Tr 4 hr - Tr Base: UT 4 Hr - UT Base | −3.4046 | 0.0007 |

The foregoing description and examples illustrate selected embodiments of the present invention. In light thereof variations and modifications will be suggested to one skilled in the art, all of which are within the spirit and purview of this invention.

What is claimed is:

1. A lipstick for freshening breath and controlling oral malodour, the lipstick comprising:

(i) from about 10 to about 99%, by weight, of lipophilic material;

(ii) from about 0.01 to about 2%, by weight, of free menthol;

(iii) from about 0.1 to about 10%, by weight, of a bound menthol substance; and (iv) from about 0.1 to about 10%, by weight, of water.

2. The lipstick according to claim 1 where the mentol bound substance is a complex of mentol with cyclodextrin.

3. The lipstick according to claim 1 further comprising anethole in a relative weight ratio of free menthol to anethole of about 20:1 to about 1.5:1.

4. The lipstick according to claim 1 wherein the bound menthol substance is menthol encapsulated within a matrix selected from the group consisting of polysaccharides, synthetic polymers and copolymers, vegetable gums and mixtures thereof.

* * * * *